United States Patent [19]

Kim et al.

[11] Patent Number: 5,429,943
[45] Date of Patent: Jul. 4, 1995

[54] **MONASCUS STRAIN, *MONASCUS ANKA* 732Y3 (KCCM 10014) PRODUCING HIGH AMOUNT OF MONASCUS PIGMENTS**

[75] Inventors: Jun-Sung Kim; Kee-Hyun Choi, both of Seoul; Jang-Youn Choi, Kyungki-do; Yoon-Soo Lee; Ik-Boo Kwon, both of Seoul, all of Rep. of Korea

[73] Assignee: Lotte Confectionery Co., Ltd., Seoul, Rep. of Korea

[21] Appl. No.: 119,343

[22] Filed: Sep. 9, 1993

[30] Foreign Application Priority Data

Oct. 26, 1992 [KR] Rep. of Korea ............... 1992-19729

[51] Int. Cl.$^6$ ........................... C12N 1/14; C12N 1/16
[52] U.S. Cl. ................................. 435/254.1; 435/41; 435/911
[58] Field of Search ........... 435/254.1, 911, 41

[56] References Cited

U.S. PATENT DOCUMENTS

| | | | |
|---|---|---|---|
| 3,765,906 | 10/1973 | Yamaguchi et al. | 426/18 |
| 4,145,254 | 3/1979 | Shepherd et al. | 435/132 |
| 4,323,648 | 4/1982 | Tanzawa et al. | 435/125 |
| 4,442,209 | 4/1984 | Miyake et al. | 435/119 |

OTHER PUBLICATIONS

Jae-Ho Lee, Kee-Hyun Choi, Jang-Youn Choi, Yoon-Soo Lee, Ik-Boo Kwon and Ju-Hyun Yu, "Enzymatic production of α-cyclodextrin with the cyclomaltodextrin glucanotransferase of Klebsiella oxytoca 19-1", *Enzyme and Microbial Technology Biotechnology Research and Reviews*, Dec. 1992, vol. 14, No. 12, Raymond E. Spier and Sheldon W. May, Editors, pp. 1017–1020.

Kim, Jun-Sung, Kee-Hyun Choi, Jang-Yoon Choi, Yoon-Soo Lee, Young-Youl Chang and Ik-Boo Kwon, "Induction of a Mutant, Monascus anka 732Y3 from Monascus anka KFCC 11832 and its Morphological Observations", *Journal of Microbiology and Biotechnology*, Jun. 1993, vol. 3, No. 2, pp. 134–138.

*Primary Examiner*—Douglas W. Robinson
*Assistant Examiner*—L. Blaine Lankford
*Attorney, Agent, or Firm*—Kenyon & Kenyon

[57] ABSTRACT

The present invention relates to *Monascus anka* 732Y3 (KCCM 10014 induced from *Monascus anka* ATCC 16360 (=IFO 4478, KFCC 11832), and more particularly is concerned with *Monascus anka* 732Y3 (KCCM 10014), which was induced from *Monascus anka* ATCC 16360 (=IFO 4478, KFCC 11832) by ultra-violet light irradiation and produces higher amounts of pigments than *Monascus anka* ATCC 16360.

1 Claim, No Drawings

MONASCUS STRAIN, *MONASCUS ANKA* 732Y3 (KCCM 10014) PRODUCING HIGH AMOUNT OF MONASCUS PIGMENTS

BACKGROUND OF THE INVENTION

1. Field of the Invention

The present invention relates to *Monascus anka* 732Y3 (KCCM 10014) induced from *Monascus anka* ATCC 16360 (=IFO 4478, KFCC 118 32) More particularly, the present invention is concerned with *Monascus anka* 732Y3 (KCCM 10014), which was induced from *Monascus anka* ATCC 16360 (=IFO 4478, KFCC 11832) by ultraviolet light irradiation and produces higher amounts of pigments than *Monascus anka* ATCC 16360.

2. Description of the Related Art

Increasing doubts about the health safety of many synthetic pigments to health has brought about a deep interest in of using natural colors in place of them. In fact, along with the trend of avoiding the usage of artificial food additives in the food industry, every effort to get safe natural pigments to take the place of artificial dyestuffs has been made although the latter have been used title to relatively cheap prices.

Recently, a great portion of the synthetic pigments have not been allowed to be used in food processes in the developed countries like America and Japan. Even the amounts of the allowed synthetic pigments that can be added to foods are restricted. Therefore, it must be recognized that it can never be too soon to find suitable natural pigments and to apply them to food processes. As natural sources for pigments, animals, plants, and microorganisms can all be taken into consideration. In the connection, the manufacture of natural pigments from animals or plants is affected by the limited amounts of the pigments, by their costs, and by the conditons of cultivation. The production of pigments by microbial processes, however, seems to hold the answer to these problems.

Historically, molds belonging to the genus Monascus have been used in the fermentative production of red wine from steamed hulled-rice and red soybean cheese in countries like China, Japan, and Indonesia. Nowadays, studies concerning the applications of pigments to food processes are actively underway in many countries.

Though the taxonomy of Monascus fungi still has much to be discussed, the following classification is generally accepted: Actinomycetes(class)-Plectomycetes(sub-class)-Aspergillaceae(family)-Monascus (genus). Hawksworth and Pitt proposed a new method for isolation and classification of Monascus sp., and classified genus Monascus into three species of *Monascus pilosus* K. Sato ex. D. Hawksw. & Pitt sp. nov., *Monascus purpureus* Went, and *Monascus rubber* van Tieghem. On the other hand, a few scientists have renamed a part of *Monascus purpureus* Went as *Monascus anka*.

The Monascus sp. is homothallic, and its life cycle is composed of asexual propagation accompanied by one-celled conidia and sexual propagation by ascospores in asci which fog in cleistothecia which develop when antheridia as male organs mate with ascogonia as female organs. According to Su's report, Monascus pigments seem to be produced more when conidia are inhibited-[Y.C.Su, Kor, J. Appl. Microbiol, Bieng., 11,325, (1983)]. Therefore, a Monascus sp. propagating sexually more often than asexually is probably effective for the hyper-production of Monascus pigments. But the factor controlling sexual and asexual propagations have not yet been discovered, nor has the role of the pigments.

The pigments produced by Monascus sp. are composed of six chemicals: rubropunctatin($C_{21}H_{26}O_5$-red color), monascorubrin($C_{23}H_{26}O_5$-red color), monascin ($C_{21}H_{26}O_5$-yellow color), ankaflavin ($C_{23}H_{30}O_5$-yellow color), rubropunctamine ($C_{21}H_{23}NO_4$-purple color), and monascorubramine($C_{23}H_{30}NO_4$-purple color).

Tadao Hiroi's test made it certain that none of aflatoxin $B_1$, $B_2$, $G_1$, and $G_2$ is produced by Monascus sp. His Amese test also represented that Monascus pigments do not work as carcinogens. Furthermore, the pigments did no harm to the animals such as rats that were fed on them[T. Hiroi, New Food Industry, 30, 1, (1988)]. As the Monascus pigments have proved to be safe to health, many researchers have begun to study the production of high amounts of them.

The inventors of the present invention, making efforts to develop a new Monascus strains capable of producing high amount of the pigments, invented *Monascus anka* 732Y3 (KCCM 100141 by irradiation of ultra-violet light upon *Monascus anka* ATCC 16360.

SUMMARY OF THE INVENTION

The objection of this invention is to induce a mutant from *Monascus anka* ATCC 16360 which can produce high amounts of Monascus pigments. More particularly, the present invention is related to a new Monascus sp., *Monascus anka* 732Y3 (KCCM 10014) capable of producing high amounts of Monascus pigments which was induced from *Monascus anka* ATCC 16360 received from the Korea Federation of Culture Collection. The mutagenesis was carried out by ultra-violet light irradiation to *Monascus anka* ATCC 16360, and then, *Monascus anka* 732Y3 (KCCM 10014) was selected.

The new strain, *Monascus anka* 732Y3 was deposited with the Korean Culture Center of Microorganisms(abbreviated KCCM) and given an accession number of KCCM 10014 by the International Depositary Authority on 18th of Aug., 1992. More particularly, the present invention

DESCRIPTION OF THE INVENTION

The observation that forms the basis of this invention is a mutant of Monascus sp. induced by UV-light irradiation that can produce high amounts of pigments. *Monascus anka* 732Y3 (KCCM 10014) was selected among the mutants induced from *Monascus anka* ATCC 16360 received from the Korea Federation of Culture Collection. *Monascus anka* ATCC 16360 and its mutants were irradiated with ultra-violet light for 2 minutes for mutagenesis. *Monascus anka* 732Y3 was, in the long run, selected from among the other mutants. When the red pigments, produced by *Monascus anka* 732Y3 (KCCM 10014) in a medium containing 7% rice powder as carbon a source and 0.3% peptone as a nitrogen source, was analyzed by a spectrophotometer at 500 nm, the absorbance was 157. The absorbance is 10 times as high as that of the red pigments produced by the parental strain, *Monascus anka* ATCC 16360. The dry cell weight of *Monascus anka* 732Y3 (KCCM 10014) was also 1.6 time higher than that of *Monascus anka* ATCC 16360.

Compared with those of its parental strain, *Monascus anka* ATCC 16360, the cultural, physiological, and morphological characteristics of *Monascus anka* 732Y3 (KCCM 10014) are represented in Tables 1, 2, 3-1 and 3-2.

TABLE 1

Cultural Characteristics of *Monascus anka* ATCC 16360 and its Mutant, *Monascus anka* 732Y3 (KCCM 10014)

| Medium | Temp. (°C.) | *M. anka* ATCC 16360 | *M. anka* 732Y3 (KCCM 10014) |
|---|---|---|---|
| CYA | 25 | colony size: 24–28 mm; colony shape: round shape; bright pink; short mycelia | colony size: 19–21 mm; colony shape: round shape; red; short mycelia |
|  | 37 | colony size: 35–44 mm; colony shape: round shape; very bright pink; very numerous short mycelia | colony size: 20–30 mm; colony shape: shapeless; dark red; a few short mycelia |
| MEA | 25 | colony size: 13–18 mm; colony shape: shapeless; yellow; long mycelia | colony size: 9–15 mm; colony shape: shapeless; orange; only a few mycelia |
|  | 37 | colony size: 20–28 mm; colony shape: shapeless; yellow; long mycelia | colony size: 4–15 mm; colony shape: shapeless; orange; only a few mycelia |
| G25N | 25 | colony size: 23–27 mm; colony shape: round shape; very bright pink; very neumerous mycelia | colony size: 17–22 mm; colony shape: round shape; red; short mycelia |
|  | 37 | colony size: 38–45 mm; colony shape: round shape; red; very numerous short mycelia | colony size: 16–21 mm; colony shape: shapeless; dark red; only a few mycelia | duration of culture: 7 days
CYA: Czapek Yeast Agar(pH 7.1); 0.3% NaNO$_3$, 0.1% KH$_2$PO$_4$, 0.05% KCl, 0.05% MgSO$_4$ · 7H$_2$O, 0.01% FeSO$_4$ · 7H$_2$O, 0.5% yeast extract, 3.0% sucrose, 1.5% agar
MEA: Malt Extract Agar(pH 5.6); 2% malt extract, 0.1% peptone, 2% glucose, 1.5% agar
G25N: Glycerol 25% Nitrate Agar(pH 7.1); 0.3% NANO$_3$, 0.1% KH$_2$PO$_4$, 0.05% KCl, 0.01% MgSO$_4$ · 7H$_2$O, 0.01% FeSO$_4$ · 7H$_2$O, 0.5% yeast extract, 2.5% glycerol, 1.5% agar

TABLE 2

Physiological Characteristics of *Monascus anka* ATCC 16360 and its Mutant, *Monascus anka* 732Y3 (KCCM 10014)

| Hydrolysis | *M. anka* ATCC 16360 | *M. anka* 732Y3 (KCCM 10014) |
|---|---|---|
| starch hydrolysis | ++ | ++ |
| fat hydrolysis | + | + |
| gelatin hydrolysis | + | + |
| casein hydrolysis | + | + |
| urea hydrolysis | +− | +− |

−: poorly done
+: well done
media: The compositions of the media used were those of Czapek Yeast Agar except sucrose, which was replaced by starch, olive oil for fat, gelatin, casein, or urea.
duration of culture: 7 days

TABLE 3-1

Morphological Characteristics of *Monascus anka* ATCC 16360 and its Mutant, *Monascus anka* 732Y3 (KCCM 10014)

| Organ | *M. anka* ATCC 16360 | *M. anka* 732Y3 (KCCM 10014) |
|---|---|---|
| hypha | + | + |
| septum | + | + |
| ascospore | + | + |
| cleistothecium | + | + |
| conidiospore | + | + |
| oidium | − | − |
| coremium | − | − |
| rhizoid | − | − |
| zygospore | − | − |
| sporangiospore | − | − |

+: existent
−: non-existent

TABLE 3-2

Morphological Characteristics of *Monascus anka* ATCC 16360 and its Mutant, *Monascus anka* 732Y3 (KCCM 10014)

| Organ | *M. anka* ATCC 16360 | *M. anka* 732Y3 (KCCM 10014) |
|---|---|---|
| quantity |  |  |
| cleistothecia | ++ | +++ |
| conidia | ++++ | ++ |
| size μm |  |  |
| cleistothecium | 37.0–75.0 | 85.0–107.0 |
| ascospore | 2.5–4.0 | 2.5–5.8 |
| conidium | 10.0–25.0 | 15.0–22.5 |

+ to ++++: a few to many
medium: potato dextrose agar(20% infusion from potato, 2% dextrose, 1.5% agar)
temperature: 30° C.
incubation period: 7 days
pH: 4.5

Although, as revealed in Table 2 and 3-1, the above two strains, *M. anka* ATCC 16360 and *M. anka* 732Y3 (KCCM 10014), have physiological characteristics similar to each other, they have different cultural and morphological characteristics. Above all, if the morphological characteristics are examined, it can be seen that the development of conidia of the mutant, *M. anka* 732Y3 (KCCM 10014), is less extensive than that of *M. anka* ATCC 16360.

Furthermore, the microscopic observation of *M. anka* 732Y3 (KCCM 10014) represented more active sexual propagation than its parental strain, which can be suggested by the larger and more numerous cleistothecia than those of *M. anka* ATCC 16360. The observation that Monascus pigments surround the cleistothecia also made it certain that the more frequent sexual propagation is developed, the more Monascus pigments are produced.

But it is not yet clear what the roles of the pigments are. Monascus pigments are, however, in some degree, related to sexual propagation because when the cleistothecia were developing, the pigments were formed around them, and because *M. anka* 732Y3 (KCCM 10014), which produces more pigments than *M. anka* ATCC 16360, develops more cleistothecia and less conidia than *M. anka* ATCC 16360.

When the new strain, *M. anka* 732Y3 (KCCM 10014) was cultivated in a medium containing 7% rice powder and 0.3% peptone, the optical density of the produced red pigments at 50 nm was 157, which was about 10 times as high as that of *M. anka* ATCC 16360. The dry cell weight of *M. anka* 732Y3 (KCCM 10014) was, at that time, 955 mg/50 ml, which was 1.6 time higher than that of *M. anka* ATCC 16360.

The distinctive feature of this invention can be found in that the new strain, *M. anka* 732Y3 (KCCM 10014), shares many common microbial characteristics with its parent, *M. anka* ATCC 16360, and in that the amount of the pigments produced is, nevertheless, far greater than that of *M. anka* ATCC 16360.

Since *M. anka* 732Y3 (KCCM 10014) produces sate and stable pigments, since the amount produced is great enough, those pigments can be considered for application to food industry, taking the place of the existing artificial pigments involving danger to health.

The following embodiment is presented to illustrate the invention and should not be regarded as limiting it in any way.

EXAMPLE

Seed medium slant containing 10% sucrose, 0.1% $KH_2PO_4$, 0.05% $MgSO_4.7H_2O$, 0.2% $NaNO_3$, 0.05% KCl, 0.001% $FeSO_4.7H_2O$, 0.3% yeast extract, 0.5% casamino acid, and 2.0% agar was innoculated with *M. anka* ATCC 16360 and placed in a 30° C. incubator for 7 days. And 10 ml of distilled water was added into the slant for suspension of the spores.

The suspended spore solution was filtered through a cotton filter in order to remove the mycelia, and diluted 10 times with sterilized distilled water. 10 ml of the diluted spore solution was poured into 9.5 cm diameter petri dishes, and ultraviolet light(100 V, 13 W) was irradiated onto the spore solution from a 40 cm distance for 2 minutes. The UV-light treated spore solution was smeared on the above seed media prepared in petri dishes, and incubated at 30°. After 7 days' incubation, one colony with relatively deep red color and relatively wide diameter was selected.

The selected colony subcultured on the above seed medium at 30° C. for 7 days was innoculated into 50 ml of pigment production medium prepared in 500 ml Erlenmyer flask containing 7% rice powder, 0.3% peptone, 0.25% $KH_2PO_4$, and 0.1% $MgSO_4.7H_2O$, and cultivated at 3° C. shaking with 120 rpm for 7 days. When the cultivation was over, for extraction of the pigments, 95% ethanol was added and shaked with 120 rpm at 30° C. for one hour. The extract was filtered through filter paper, and the filtrate was applied to spectraphotometer for determination of the amounts of produced red and yellow pigments at 500 nm and 400 nm, respectively.

TABLE 4

| Strain | Pigment production by *M. anka* 732Y3 (KCCM 10014) and *M. anka* ATCC 16360 | | Dry Cell Weight (mg/50 ml) |
|---|---|---|---|
| | Optical Density of Produced Pigments | | |
| | $A_{500}$ (red pigments) | $A_{400}$ (yellow pigments) | |
| *M. anka* ATCC 16360 | 15.9 | 21.1 | 604 |
| *M anka* 732Y3 (KCCM 10014) | 157.9 | 148.0 | 955 |

Through the above experiment, *Monascus anka* 732Y3 (KCCM 10014) was eventually selected, and compared with those of the parental strain, *Monascus anka* ATCC 16360. The amount of the produced red pigments and the dry cell weight of *M. anka* 732Y3 (KCCM 10014) are presented in Table 4.

Results of these experiments demonstrate that sexual propagation is closely related to production of the pigments by the Monascus species. The growth of *Monascus anka* 732Y3 (KCCM 10014) was observed to depend more on sexual propagation than that of its parental strain, *Monascus anka* ATCC 16360. Furthermore, it could be seen that a ring of pigments is developed around cleistothecia of *M. anka* 732Y3.

What is claimed is:

1. A strain of *Monascus anka* KCCM 40014.

* * * * *